United States Patent
Zhang et al.

(10) Patent No.: US 9,421,420 B2
(45) Date of Patent: Aug. 23, 2016

(54) WELLNESS/EXERCISE MANAGEMENT METHOD AND SYSTEM BY WELLNESS/EXERCISE MODE BASED ON CONTEXT-AWARENESS PLATFORM ON SMARTPHONE

(71) Applicant: Futurewei Technologies Inc., Plano, TX (US)

(72) Inventors: Jianyu Zhang, San Jose, CA (US); Chia Chin Chong, Santa Clara, CA (US)

(73) Assignee: Futurewei Technologies, Inc., Plano, TX (US)

( * ) Notice: Subject to any disclaimer, the term of this patent is extended or adjusted under 35 U.S.C. 154(b) by 0 days.

(21) Appl. No.: 14/500,842

(22) Filed: Sep. 29, 2014

(65) Prior Publication Data

US 2015/0087478 A1 Mar. 26, 2015

Related U.S. Application Data

(63) Continuation-in-part of application No. 14/468,298, filed on Aug. 25, 2014.

(60) Provisional application No. 61/869,525, filed on Aug. 23, 2013, provisional application No. 61/883,904, filed on Sep. 27, 2013, provisional application No. 61/883,907, filed on Sep. 27, 2013.

(51) Int. Cl.
| | | |
|---|---|---|
| *A63B 24/00* | (2006.01) | |
| *G09B 19/00* | (2006.01) | |
| *G06F 19/00* | (2011.01) | |

(52) U.S. Cl.
CPC ....... *A63B 24/0003* (2013.01); *G06F 19/3481* (2013.01); *G09B 19/00* (2013.01); *G09B 19/0038* (2013.01)

(58) Field of Classification Search
CPC .............. A63B 24/00; A63B 24/0003; A63B 24/0062; G09B 19/00; G09B 19/0038; G09B 19/3481

IPC .............. A63B 24/00, 24/0062, 21/015, 21/00, A63B 22/00

See application file for complete search history.

(56) References Cited

U.S. PATENT DOCUMENTS

| | | | |
|---|---|---|---|
| 5,067,710 A * | 11/1991 | Watterson | A63B 21/015 434/247 |
| 2006/0040793 A1* | 2/2006 | Martens | A61B 22/00 482/8 |
| 2006/0205564 A1 | 9/2006 | Peterson | |
| 2007/0219059 A1* | 9/2007 | Schwartz | A61B 5/0205 482/8 |
| 2010/0056340 A1 | 3/2010 | Ellis et al. | |
| 2011/0172060 A1 | 7/2011 | Morales et al. | |
| 2011/0251021 A1* | 10/2011 | Zavadsky | A63B 21/00 482/5 |
| 2011/0281687 A1 | 11/2011 | Gilley et al. | |
| 2012/0313776 A1 | 12/2012 | Utter, II | |
| 2013/0013331 A1 | 1/2013 | Horseman | |
| 2013/0194066 A1 | 8/2013 | Rahman et al. | |
| 2015/0056589 A1 | 2/2015 | Zhang et al. | |
| 2016/0007885 A1* | 1/2016 | Basta | A61B 5/112 482/5 |

OTHER PUBLICATIONS

"U.S. Appl. No. 14/468,298, Non Final Office Action mailed Feb. 4, 2016", 6 pgs.

* cited by examiner

*Primary Examiner* — Glenn Richman
(74) *Attorney, Agent, or Firm* — Schwegman Lundberg & Woessner, P.A.

(57) ABSTRACT

A device, method and system provide a wellness management process and/or an exercise management process for use with a smartphone or other mobile computing device. Various data about the user is obtained and used for determining and recommending an action or exercise to the user to improve the user's wellness/physique/health. The action determined can be based on: (1) current biometric and/or motion data about the user (from the sensors), and (2) current physical condition(s), such as health/medical information or condition about the user (from the user's personal information, e.g., health library or programmed into the smartphone). Specific information about the user is taken into consideration when recommending user action or exercise, such as the user's specific physical, health or medical conditions.

17 Claims, 3 Drawing Sheets

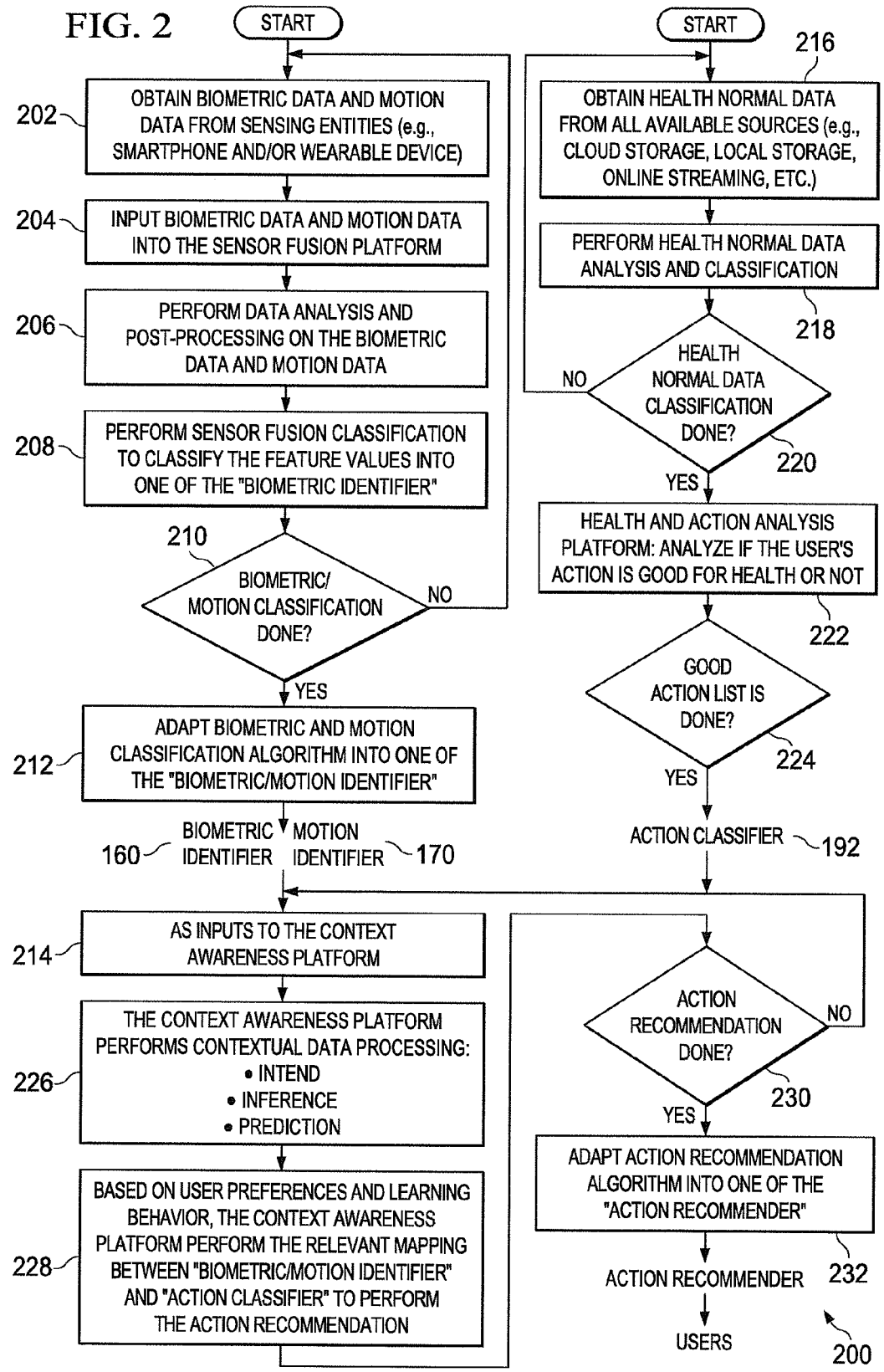

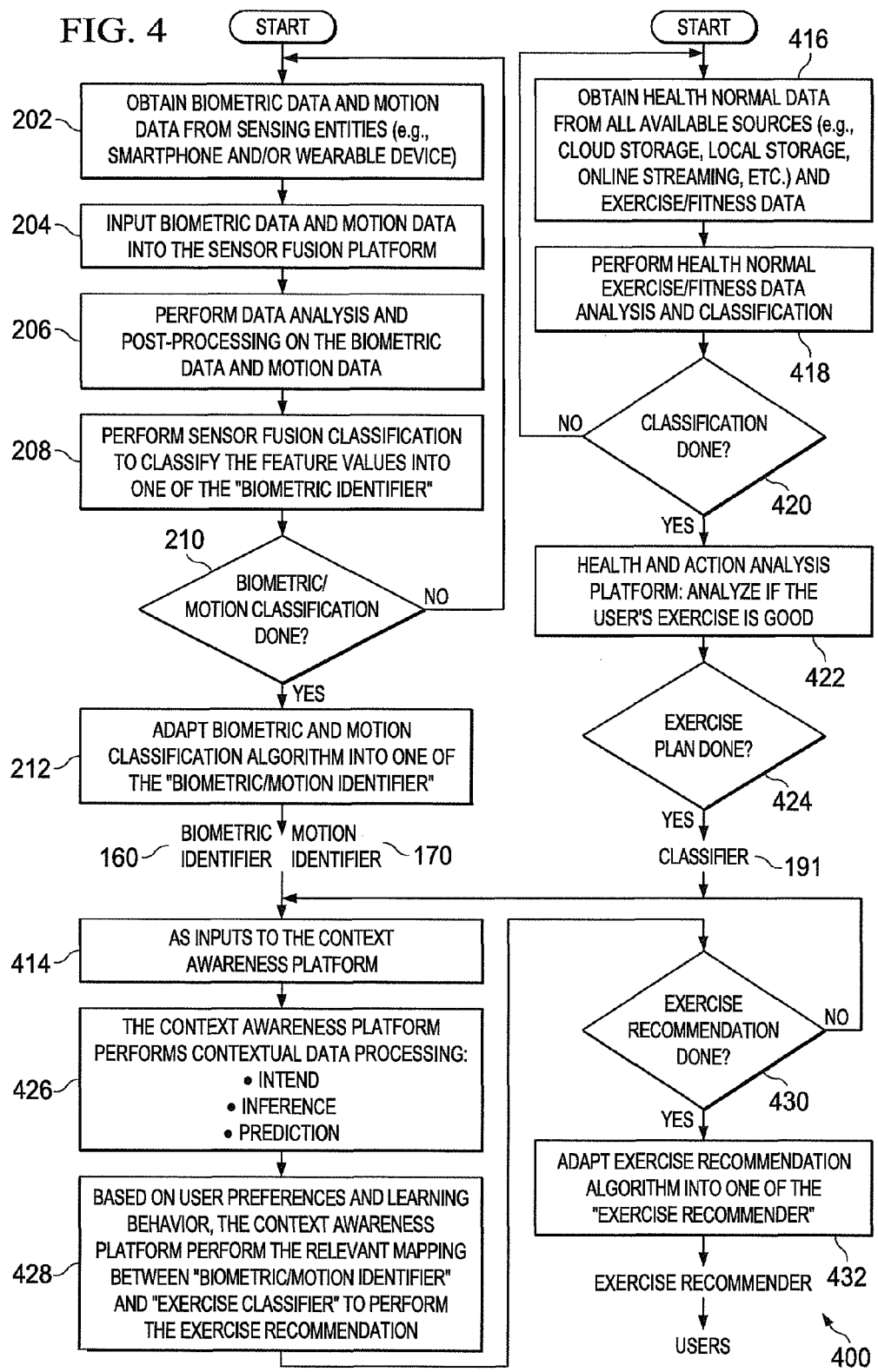

WELLNESS/EXERCISE MANAGEMENT METHOD AND SYSTEM BY WELLNESS/EXERCISE MODE BASED ON CONTEXT-AWARENESS PLATFORM ON SMARTPHONE

CROSS-REFERENCE TO RELATED APPLICATIONS

The present application is a continuation-in-part of and claims priority to U.S. non-provisional patent application Ser. No. 14/468,298 filed on Aug. 25, 2014, which claims priority to U.S. provisional Application No. 61/869,525 filed on Aug. 23, 2013, and which are incorporated herein by reference. The present application also claims priority to U.S. provisional patent Application No. 61/883,904 filed on Sep. 27, 2013 and U.S. provisional patent Application No. 61/883,907 filed on Sep. 27, 2013, both of which are also incorporated herein by reference.

TECHNICAL FIELD

The present disclosure relates generally to health and exercise wellness, and more particularly to a method and system for wellness/exercise management based on a context awareness platform on a mobile electronic device, such as a smartphone.

BACKGROUND

Health and wellness are becoming more and more important as individuals devote more time to generally non-physical activities, such as work at an office or on a computer. Because a person often performs these activities with little or no physical exertion, such activities are generally bad for a person's overall health and wellness. Similarly, when an individual does engage in some form of physical activity that requires physical exertion, oftentimes the individual overexerts themselves. Such activities are also generally detrimental for a person's overall health and wellness. Further, an individual's situation dynamically changes over time, which could be as short as (or shorter) a day. For example, an individual might not be able to perform the same exercise he did yesterday due to achieving much less sleep the night before. Therefore, it may be desirable to adjust the individual's exercise plan timely and automatically.

Various activities recommendation systems/services exist in the marketplace—which recommend or remind a person to engage in some physical activity or exercise for physical fitness. However, these systems/services do not ascertain, determine or recognize automatically the person's current physical situations or condition (or capabilities), such as health/medical conditions and most recent activity history, and generate a recommendation for health/wellness, and notify the person. Further, such systems are not capable of being disabled when desirable in some scenarios, such as when the person is attending a meeting. One prior art system is a simple alarm tool. These must be set up manually by the user and do not take into consideration the user's physical situation or past physical activity history.

More particularly, none of the activity recommendations systems/services automatically recommend wellness activities to a user based on the user's physical motion sensed or determined (or inferred) from sensors (e.g., motion sensors) or based on the user's biological state sensed or determined (or inferred) from sensors (e.g., biometric sensors) using a mobile smartphone or other mobile device, where the sensors may be co-located within the mobile device or located on the person and communicatively coupled to the mobile device.

SUMMARY

In one embodiment, there is provided a method for recommending an action to a user for enhancing wellness or health of the user. The method includes receiving first data from a first sensor configured to sense motion of a user and second data from a second sensor configured to sense biometric data of the user, processing the received first and second data and identifying a type of activity engaged in by the user, determining a recommended action to be performed by the user in response to the identified type of activity and a current health/medical condition of the user, and notifying the user of the recommended action.

In another embodiment, there is provided a mobile wearable device for sensing one or more physical attributes of a user associated with the device and recommending an activity to the user for enhancing wellness of the user. The device includes one or more sensors configured to sense one or more physical attributes of the associated user and output physical attribute information and a processor configured to: receive the physical attribute information, identify the user's type of activity based on the received physical attribute information, determine a recommended action to be performed by the user in response to the identified type of activity and a current health/medical condition of the user, and notify the user of the recommended action.

In one embodiment, there is provided a method for recommending an action to a user for enhancing wellness or health of the user. The method includes receiving first data from a first sensor configured to sense motion of a user; receiving second data from a second sensor configured to sense biometric data of the user; processing the received first and second data and identifying a type of activity the user is currently conducting and a current physical condition of the user; determining a recommended action to be performed by the user in response to the identified type of activity and the current physical condition of the user; and notifying the user of the recommended action.

In yet another embodiment, there is provided a method for recommending a change in a user's current exercise activity for enhancing physical attributes and health of the user. The method includes receiving first data from a first sensor configured to sense motion of a user, receiving second data from a second sensor configured to sense biometric data of the user, processing the received first and second data and identifying a type of activity engaged in by the user and a current physical condition of the user, determining a recommended change to the user's current exercise activity in response to the identified type of activity and the current physical condition of the user, and notifying the user of the recommended change.

In another embodiment, there is provided a mobile wearable device for sensing one or more physical attributes of a user associated with the device and recommending a change in the user's current exercise activity. The device includes one or more sensors configured to sense one or more physical attributes of the associated user and output physical attribute information and a processor. The processor is configured to receive the physical attribute information, identify the user's type of activity and a current physical condition at least in part based on the received physical attribute information, determine a change in an exercise plan of the user in response to the identified type of activity and the identified current physical condition of the user, and notify the user of the change.

In still another embodiment, there is provided a method for recommending an action to a user for use in a user's current exercise activity to enhance physical attributes and health of the user. The method includes receiving, by a device wearable by the user, first data from a first sensor configured to sense motion of a user; receiving, by the device, second data from a second sensor configured to sense biometric data of the user; processing, by the device, the received first and second data and identifying a type of activity engaged in by the user and a current physical condition of the user; determining, by the device, a recommended change to the user's current exercise activity in response to the identified type of activity and the current physical condition of the user; and notifying, by the device, the recommended change to the user.

BRIEF DESCRIPTION OF THE DRAWINGS

For a more complete understanding of the present disclosure, and the advantages thereof, reference is now made to the following descriptions taken in conjunction with the accompanying drawings, wherein like numbers designate like objects, and in which:

FIG. 2 illustrates a flowchart of a wellness management process in accordance with disclosed embodiments that may be performed by the system of FIG. 1;

FIG. 4 illustrates a flowchart of an exercise management process in accordance with disclosed embodiments that may be performed by the system of FIG. 1.

DETAILED DESCRIPTION

Figure 1:
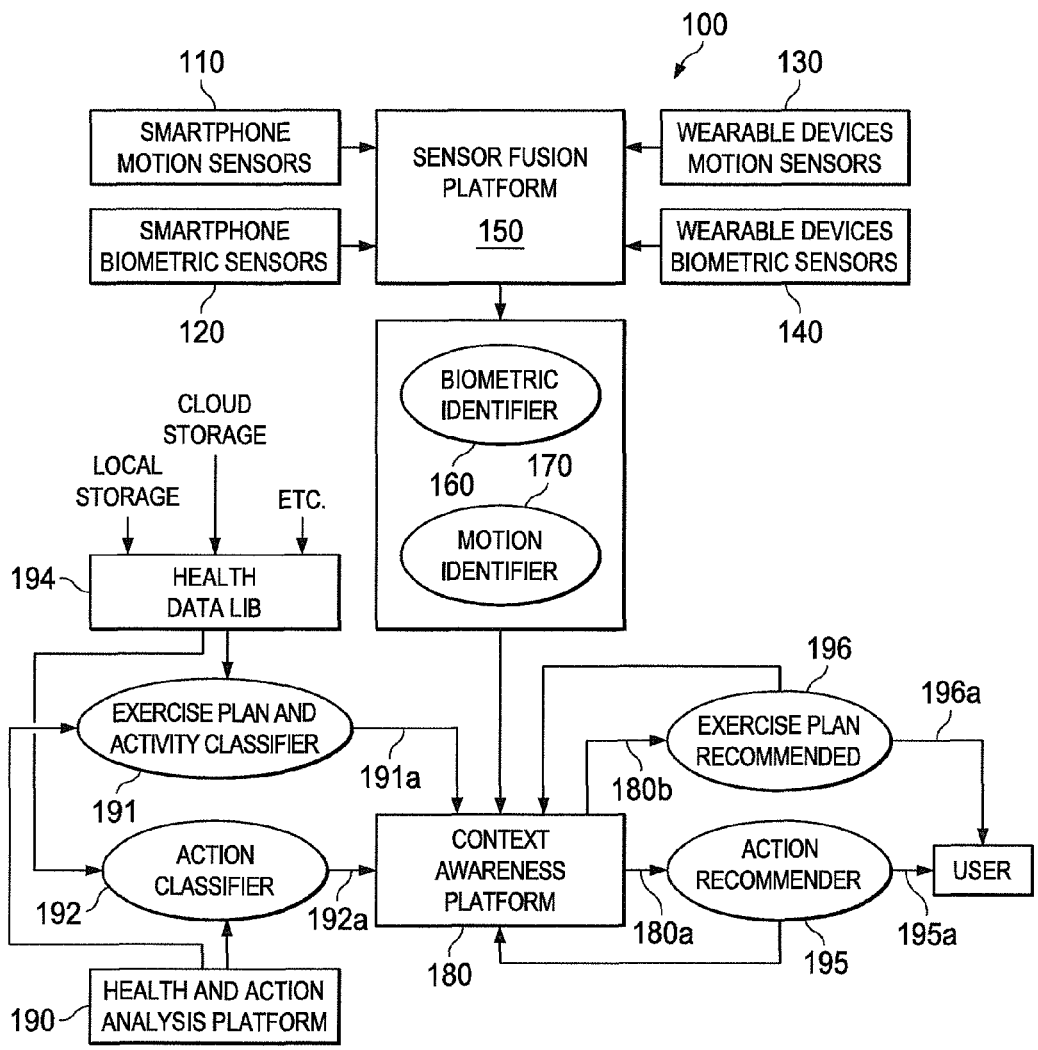
FIG. 1 illustrates a system for wellness management based on a context awareness platform or process within a mobile electronic device in accordance with the present disclosure.

The present disclosure describes methods and systems for wellness management and/or exercise management of a person.

In general terms, wellness management is directed to managing activities designed or intended to reduce negative impacts on a person's health caused by some event, activity or characteristic. For example, and in accordance with the present disclosure, wellness management may include recommending/notifying ("activity recommendation") a user to modify or change the physical activity(ies) in which the user is currently engaged to reduce negative impacts. For example, the system may notify or remind the user to go the restroom or get up and walk around if he/she has been sitting for a long period of time. Another example would be reminding the user to take medicine (prescribed or not) if he/she has a cold and has not taken any medicine. This is the result of context-awareness computing that obtains or retrieves data from various data sources, including but not-limited to: sensors (biometric, motion, etc.), smartphone basic applications (e.g., date for doctor appointment in the calendar application with note "see doctor for cold"), applications provided by hospitals or doctor offices (e.g., record of doctor visit), and wearable device(s) providing some health/medical features. Context-awareness computing or processing assesses this data and generates a presumption or prediction based on the data. Various context-based computing or processing methods or techniques are known in various fields, and can be utilized herein. Wellness management systems and methods will assist the user in improving his/her wellness and health.

On the other hand, exercise management is directed to managing activities designed and intended to increase physical attributes/characteristics (e.g., strength, stamina, size, etc.) of a person, while at the same time reduce negative impacts. This may include modifying or changing a user's exercise plan to reduce potential negative impacts, such as when a user is engaging in too heavy exercise under their current situation, and/or increase their physical attributes if a user is engaging in too little exercise for the plan under their current situation. Exercise management can change a user's exercise plan, but it also changes his/her current action. Exercise management mainly occurs when a user is dedicated or directed exercising. Provide the most suitable plan for the users based on his situation and context awareness computing.

For example, and in accordance with the present disclosure, exercise management may include recommending/notifying ("activity recommendation") a user to perform certain exercises or physical activities based on the user's current physical situation, such as when the user has not engaged in, or is insufficiently engaging in, physical activity during the day. For a more specific example, when the user is running and the system detects the user's heartbeat is relatively slow and motion is slow, the disclosed system may recommend/notify the user to increase running speed in order to achieve an increased heartbeat, etc. Exercise management systems and methods will assist the user in improving his/her physical characteristics and health. In another specific example, when the user is running and the system detects the user's heartbeat is too fast or body temperature is too high, the disclosed system may recommend/notify the user to slow down or stop for a period of time. Similarly, if the system detects the user's heart rate is too high or too low, the system may automatically adjust the user's exercise plan to match the user's current situation.

In addition, an exercise plan may be developed and recommended to a user after assessing and determining their wellness and situation.

While "wellness" and "exercise" are generally defined above, these two terms are not clearly mutually exclusive—and some activities may be directed to, or provide, both wellness and exercise benefits to a person. For example, if a person has been generally stationary for a significant period of time, the user may be notified and recommended to perform some physical activities (e.g., moving, walking, etc.). As will be appreciated, this scenario could be considered both wellness and exercise. Usually, when the user is exercising under a plan, it is mainly directed to exercise, but may include some element(s) of wellness (if exercising too much, notified to slow down).

The present disclosure also describes a method and system that process data about the user, and determines and recommends a wellness/exercise/health action to a user. Throughout the present disclosure, the term "action" is a general term and can apply actions intended to provide wellness (reduce negative impacts) or exercise benefits, or both. The term "exercise" generally distinguishes those actions intended primarily to provide exercise benefits (i.e., increase or improve physical attributes/characteristics).

In one embodiment, a recommended action is determined based on: (1) current biometric and/or motion data about the user (from the sensors); and (2) current physical condition(s)

or situation about the user, such as a user's current health/medical condition (from the user's personal information, e.g., health library or programmed into the smartphone). Other prior art systems appear limited to recommending "some" physical activity simply for "physical fitness" purposes, in general. These physical fitness activities are general in nature (cardiovascular, exercise, lifting weights, reducing inactivity, etc.) and are simply intended to increase physical strength and/or stamina without any assessment whether these activities are indeed being performed (or performed correctly) or taking into account the users current physical situation/capability. The present disclosure (in some embodiments) also takes into consideration specific information about the user when recommending user action, such as the user's physical conditions, such as one or more specific health or medical conditions when making a recommendation.

In addition, in other embodiments, the present disclosure may recommend user action that is not directly related to improving the user's physical strength, etc. Instead, the recommended action may be to reduce physical activity in order to alleviate or reduce health risks associated with the user's current medical/health situation. The presence of a medical condition/health specific to the user may also result in different recommend user actions other than simply "more physical activity." Examples of recommended actions may be: call the doctor, take more vitamins, reduce physical activity, make more frequent trips to the bathroom, drink more fluids, consume more/less sugar, etc. These are examples of a recommended "action" that is primarily directed to wellness.

Another embodiment of the present disclosure ascertains and utilizes general health rules (from health industry and knowledge) to assist in recommending an action that reduces the current health risk to the user based on the user's current situation and/or activity(ies).

In other embodiments, the system automatically generates the activity reminder or activity recommendation for an "action" (or "exercise") based on the user's current physical activity and physical attribute(s), and may further be based on recent historical physical activity and attribute(s) and/or common health rules (knowledge library) and exercise/fitness rules.

Information about the user's physical activity is based on data collected from one or more motion sensors (e.g., accelerometers, gyroscopes, position or location sensors, pressure sensors, etc.), while information about the user's physical attribute(s) is based on data collected from one or more biometric sensors (e.g., a sensor configured to detect a biometric parameter). A biometric parameter is any biological phenomenon exhibited by a person, body or a surrounding environment. In one embodiment, the sensors may be embedded in mobile device (e.g., a smartphone) carried by the user. In another embodiment, the sensors may be physically separate from the mobile device, but physically attached or affixed to the user's body, and further in communication with the mobile device. Another embodiment may provide for a combination thereof.

The activity reminder and action recommendation systems and methods may include a learning system for improving accuracy in the identification of the physical activity(ies) engaged in and what activity or action is recommended to be performed. In addition, if a user is required to be in a stationary mode for a period of time longer than a predetermined reminder threshold (e.g., in a meeting), the system may be overridden and disabled either manually by the user or automatically. For example, in the event the user is in a meeting, the system can detect this situation (e.g., by the user's calendar, by the user's location, etc.) and automatically disable or override the system or reminder. In addition, the functionality of a wellness mode or exercise mode can be disabled or enabled by a user manually.

The systems (and methods) described herein include a sensor fusion platform which collects raw data from the sensors (motion and/or biometric—as described above). The raw data is processed and the system determines or infers the user is engaging in certain physical (or generally non-physical) activity or activities. From this data, the user's physical activity is determined and classified into one or more physical activity categories, such as sitting, walking, running, driving, etc. These may be referred to herein as a "motion identifier" or "activity identifier." In addition, different biological states of the user (physical attributes) can be determined and classified into biological state categories, such as perspiration level, heartbeat, body temperature, etc. These may be referred to herein as a "biometric identifier" or "biological state identifier."

The system also includes a context awareness platform for receiving as input the motion and biometric identifiers and automatically generates a "recommended action." This recommended action may include an activity reminder and/or an activity recommendation (as described above). As will be appreciated, the recommended action may further be a "recommended exercise" or "exercise plan."

One benefit of the methods and systems described herein is to provide an automatic reminder/recommendation to the user to engage in or perform some physical activities after being in a relatively stationary mode for an extended period of time. Another benefit is to provide an automatic recommendation/notification to the user to modify his or her current physical activity in the event the user is over/under exerting himself or herself, or to perform some recommended action due to the user's specific medical/health condition coupled with the user's current biometric/motion situation. This will help the user improve his/her wellness, exercise and/or health.

Now turning to FIG. 1, there is illustrated a block diagram of a physical activity or action recommendation system 100 in accordance with the present disclosure. In this example embodiment, the system 100 includes one or more motion sensors 110 associated with a mobile electronic device (e.g., smartphone), one or more biometric sensors 120 associated with a mobile device (e.g., the smartphone), one or more motion sensors 130 associated with a wearable device and one or more biometric sensors 140 associated with (the same or a different) wearable device. As will be appreciated, although multiple sensors are shown, the system 100 may include a different number of sensors, and the sensors may be associated with the mobile electronic device only, the wearable device only or in any combination thereof. Other sensors could be incorporated into the system.

The system 100 further includes a sensor fusion platform or process 150 that receives biometric and/or motion sensor data from one or more of the sensors 110, 120, 130, 140 and analyzes and processes the received data to classify or generate a biometric identifier 160 and/or a motion identifier 170. The generated biometric identifier 160 and motion identifier 170 are input to a context awareness platform or process 180.

The context awareness platform or process 180 receives as an input an "action-health list" or "good action list" 192a from an action classifier process 192 relating to different physical activities. The action classifier process 192 receives personal user health information and common health rules from a health and action analysis platform or process 190. The action classifier 192 uses known health information about the user (this may be obtained from external sources and databases, such as the user's health data library 194) and common health rules to generate the good action list. The user's health data library 194 includes the user's personal health data, such as whether the user has high blood pressure, etc. The health and action analysis platform 190 obtains health research and medical information from various sources relating to common health rules, such as a person with high blood pressure should also have a high heart rate.

Based on the common health/medical rules from platform 190 and the user's personal health data from the health library 194 (collectively, health/medical information), the action classifier process 192 generates the good action list 192*a* for the user. For example, the good action list 192*a* may include the following items in the list: the user should reduce activity to keep his/her heart rate under a predetermined threshold (e.g., 150/min). Therefore, reducing activity is a good healthy action when the user's heart rate is higher than 150/min. As will be appreciated, there may exist many common health rules and various personal health data for processing, and the action classifier process 192 may generate multiple good action list items. Persons of ordinary skill in the art will understand that various suitable common health rules and different types of personal health data may be input and utilized in the system to generate different good action list items.

As described herein, the terms "health/medical" or "health/fitness" are meant to include health, medical and/or fitness (and not limited to only the two terms utilized).

It will be appreciated that the good action list 192*a* may be generated initially based on current personal health data and current common health rules available. This process 192 is performed dynamically, but may not necessarily be performed on an hourly or even daily basis—as a person's personal health data usually does not change that often. For example, the good action list could be generated and updated periodically, such as every week or month. Also, the entire list may be re-generated, or only particular items in the current list may be updated. Additionally, the process 192 may be performed upon start-up of the system, and the good action list items will be stored in memory. Alternatively, the good action list items could be generated remotely and pre-stored in memory, and then updated periodically.

In addition to input(s) from the action classifier process 192, the context awareness platform or process 180 may also receive as an input an "exercise plan" or activity 191*a* from an exercise plan and activity classifier process 191 relating to different exercise(s) and exercise plans. Like the process 192, the process 191 may receive personal user health information, common health rules, and exercise/fitness rules and other information from the health and action analysis platform 190. The exercise plan and activity classifier 191 uses known health information and/or exercise information about the user (this may be obtained from external sources and databases, such as the user's health data library 194), common health rules, exercise rules and exercise information to generate the exercise plan. The health and action analysis platform 190 may also obtain exercise and fitness information from various sources relating to exercise, fitness and health rules, such as a person with high cholesterol should engage in cardiovascular activities (e.g., running, rowing, basketball, etc.) for at least 30 minutes achieve the goal: burn fats. This information can be obtained from various readily available sources, e.g., research centers, such as Nike/Adidas related labs, medical institutions, and other medical/health knowledge sources.

Based on the common health/medical rules and exercise/fitness rules and information from platform 190 and the user's personal health data from the health library 194 (collectively, health/medical information), the exercise plan and activity process 191 generates the exercise plan or activity 191*a* for the user. For example, the exercise plan or activity 191*a* may include a running activity for X minutes and keep heart rate at (or under, or above) Y per minute. As will be appreciated, it is desirable to keep heart rate at a relatively fixed rate for a period of time (which rate is related with age.

It will be understood that there may exist many common health rules, fitness/exercise rules and information, and various personal health data for processing, and the action classifier process 191 may generate multiple exercise plans or activities. Persons of ordinary skill in the art will understand that various suitable common exercise/fitness rules and information may be additionally input and utilized in the system to generate different exercise plans and/or activities.

The exercise plan and activity 191*a* may be generated initially based on current personal health data, current common health rules available and/or current common exercise/fitness rules and information. Similar to process 192, the process 191 is performed dynamically, but may not necessarily be performed on an hourly or even daily basis—as a person's personal health data and/or exercise/fitness rules usually does not change that often. For example, the exercise plan 191*a* could be generated and updated periodically, such as every week or month. Also, the entire plan may be re-generated, or only particular items in the current plan may be updated. Additionally, the process 191 may be performed upon start-up of the system, and the exercise plan will be stored in memory. Alternatively, the exercise plan 191*a* could be generated remotely and pre-stored in memory, and then updated periodically.

With these data inputs (e.g., user's good action list 192*a*, motion identifier(s) 170 and biometric identifier(s) 160), the context awareness platform 180 processes the data and performs a mapping between the biometric identifier(s) 160 and/or motion identifier(s) 170 and the good action list 192*a* in order to generate a list of possible actions 180*a* based on activities and conditions. The following provides two examples of actions for the user (based on activities and conditions):

[IF] user heart rate is higher than 150/min and is exercising (and the user's heart rate should be higher than 140/min under the user's exercise plan),
[THEN] recommend that user reduce activity; or
[IF] user heart rate is higher than 150/min and is not exercising, [THEN] recommend that user call doctor.

With the user's current biometric identifier(s) 160 and motion identifier(s) 170, an action recommender process 195 consults the list of actions and determines what activity(ies) or action(s) 195*a* should be recommended to the user. For example, assuming the user's current motion identifier 170 indicates "running" (or exercise) and the current biometric identifier 160 indicates heart rate equal to 160, the action recommender process 195 maps or compares the user's current motion/biometric data against the list of good actions and determines a recommended activity or action.

With these data inputs (e.g., user's exercise plan and activity 191*a*, motion identifier(s) 170 and biometric identifier(s) 160), the context awareness platform 180 processes the data and performs a mapping between the biometric identifier(s) 160 and/or motion identifier(s) 170 and the exercise plan 191*a* in order to generate a list of possible actions 180*b* based on activities and conditions. The following provides two examples of actions (exercise-based) for the user (based on activities and conditions):

Example 1

[IF] user heart rate is higher than 150/min and is exercising and the exercise plan calls for exercising one hour, and (i) the user had a lower amount of sleep than normal the night before or (ii) right now the user's current physical condition is unhealthy or bad,

[THEN] recommend the user change his exercise plan (for example: change one hour exercising to one-half hour of exercising for that day).

Assumption: User's heart rate should be 140/min according as his physical attributes.

Example 2

[IF] user heart rate is higher than 150/min, the user is exercising, and the exercise plan calls for running one hour, and (i) right now the user's physical condition is healthy or good,

[THEN] recommend the user change his exercise plan (for example: change running to walking or reduce the user running rate, but still be for one hour).

Assumption: User's heart rate should be 140/min according as his physical attributes.

As will be understood, unhealthy or bad physical conditions are described as the user being unusually tired, weak, or exhausted—due to insufficient or poor sleep or recovering from an illness. There are times when a user cannot readily comprehend this condition, but the device(s), method(s) and systems described herein provide the capability and functionality to determine this condition. For example, if a user normally achieves a heart rate of 150/min after a 30-minute exercise, but now achieves that same heart rate after only 10 minutes and/or the sensors detect higher sweat levels (more than normal) and/or higher blood pressure levels (more than normal), the device determines or presumes (using context-awareness computing or processing) the user has an unhealthy or bad physical condition at that time.

Similarly, healthy or good physical conditions are described as the user being full of energy, having good endurance, etc.—perhaps due to sufficient sleep and not recovering from an illness.

With the user's current biometric identifier(s) 160 and motion identifier(s) 170, an exercise recommender process 196 consults the exercise plan and activity 191*a* and determines what activity(ies), action(s), exercise plan (or change to current exercise plan) 196*a* should be recommended to the user. For example, assuming the user's current motion identifier 170 indicates "running" (or exercise) and the current biometric identifier 160 indicates heart rate equal to 110, the action recommender process 196 maps or compares the user's current motion/biometric data against the exercise plan and activity 191*a* and determines a recommended activity or action. For example, because the user is running, the motion identifier indicates running slowly, and the biometric identifier indicates a low heart rate, the recommended exercise action may be to increase running speed.

In either process (wellness management process or exercise management process), the recommended user action 195*a* or 196*a* is automatically delivered to the user (e.g., through an I/O device in the mobile device, such as a display or speaker). As will be appreciated, multiple biometric identifiers and motion identifiers may be factors in determining a recommended user action. In addition, more than one user action may be recommended. As will be appreciated, the described wellness management process and exercise management process may be performed separately, in parallel, or otherwise in conjunction with each other.

In one embodiment, the platforms or processes 150, 180, 190, 191, 192, 195 and/or 196 are included within or performed by the mobile electronic device including the sensors 110, 120. As will be appreciated, the mobile electronic device includes a processor or processing system, memory, various input/output devices, including for communication (wireless, wired) with any external motion sensors, such as motion sensors 130, 140, and a display. One or more software application programs (software, firmware, code) are utilized to perform the actions or provide the functions of the platforms or processes 150, 180, 190, 191, 192, 195 and/or 196 described herein.

In another embodiment, all or part of the platforms and processes 180, 190, 191 and 192 may reside in a server-type processing device or system physically separate from the mobile device, and the mobile device transmits the sensor data to the server-type processing device. This transmission may be done by communications via wireline, wireless or combination thereof. In yet other embodiments, one or more of the platforms or processes may be incorporated within the mobile electronic device and one or more may reside external to the device.

FIG. 2 illustrates a flowchart of a process 200 in accordance with disclosed embodiments performed by the system 100 of FIG. 1. The process 200 illustrates one embodiment of a wellness management process contemplated by the present disclosure.

The system 100 obtains biometric data and motion data from one or more sensing entities (step 202). For example, the system 100 may obtain the biometric data and the motion data from one or more of the sensors 110, 120, 130, 140. The terms "obtain" or "obtaining" as used herein, can include loading from a storage device, receiving from another device or process, receiving via an interaction with a user, and are not limited to any specific method or way, unless expressly stated.

The system 100 inputs the raw biometric data and the raw motion data into the sensor fusion platform or process 150 (step 204). For example, the sensor fusion platform 150 receives biometric and/or motion data generated from the one or more of the sensors 110, 120, 130, 140.

The sensor platform 150 performs data analysis and post-processing on the biometric data and the motion data (step 206) to categorize the user's current activity/condition. This may include a sensor classification operation to classify the sensor data into one or more biometric identifiers and/or motion identifiers (step 208). For example, the sensor platform 150 analyzes and processes the received sensor data to classify or generate the user's current biometric identifier(s) 160 and/or the motion identifier(s) 170. For example, motion identifiers 170 may identify the motion as sleeping, sitting walking, running, driving, etc. Examples of biometric identifiers 160 may include heart rate, body temperature, respiratory rate, etc. More than one type of activity may be determined or identified. As will be appreciated, various methods and processes are known to those of ordinary skill in the art for determining the type of activity based on motion sensor data and/or biometric sensor data. Though a few examples are described, different and additional motion identifiers and biometric identifiers can be determined and used in the system 100.

A determination of whether biometric and/or motion classification is complete is made (step 210). For example, the acquisition of the sensor data and determination classification may be performed one time or multiple times periodically, and may also be performed over an extended period of time (e.g., second, minute, hours) depending on the desired application and likely activities. The frequency and timing of the sensor data acquisition and identifier determination may be based on the user's current health data (e.g., what health conditions the user may have). If incomplete, the process reverts to step 202. If complete, then a biometric and motion classification process results in the generation of the one or more biometric identifiers 160 and/or the motion identifiers 170 (step 212). The generated biometric identifier(s) 160 and motion identifier(s) 170 are input to the context awareness platform 180 along with the good action list 192a (step 214) and further processed.

The good action list 192a is generated from known health normal information about various physical activities and user-specific health information (as described more fully above). For example, the process may obtain the user's health information (step 216) from external sources and databases, such as from the health data library 194 (cloud storage, local storage, online streaming, etc.). In addition, health normal information is obtained from various sources (as described above). Health data analysis and classification is performed (step 218). This step may classify the user into a medical/health category based on various factors. For example, the user may be classified as diabetic, high cholesterol, high blood pressure, or any other medical condition that may affect the user's health or wellness. A determination of whether health data classification is complete is made (step 220). If incomplete, then the process 200 reverts to step 216. If complete, then the health and action analysis platform 190 determines the good action list 192a (step 222). The health and action analysis platform 190 obtains health research and medical information from various sources relating to common health rules, such as a person with high blood pressure should also have a high heart rate. The health and action analysis platform 190 provides rules to the action classifier process 192 which determines the good action list 192a (step 222) computed by the inputs from 190 and 194. The good action list 192a is input to the context awareness platform 180.

With the inputs shown, the context awareness platform 180 performs contextual data processing (step 226). Mapping between the received biometric/motion identifier(s) and the good action list 192a is performed (step 228). For example, the context awareness platform 180 processes the data (good action list 192a and sensor identifiers 160, 170) and generates a mapping between the biometric identifier 160 and/or the motion identifier 170 and the good action list 192a to determine an action recommendation. In another embodiment, the system may learn facts or behavior of the user, and the user action(s) recommended may be based at least in part on the user' past or learned behavior.

A determination of whether the action recommendation process is complete is made (step 230). If incomplete, the system reverts to step 214. If complete, the action recommendation process is performed by the action recommender 195 (step 232) and one or more recommended actions is determined. The recommended action 195a is delivered or notified to the user (e.g., through an I/O device in the mobile device, such as a display or speaker) or some other method of notification using the device.

Figure 3:
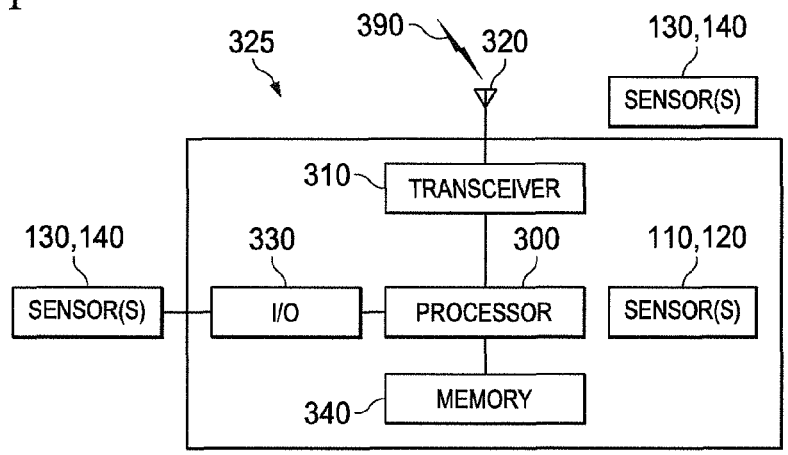
FIG. 3 illustrates an overall block diagram of an example mobile electronic device in accordance with disclosed embodiments.

Turning now to FIG. 3, there is shown an overall block diagram of an example mobile electronic device 325 (e.g., smartphone) implementing the system 100 described herein. As will be appreciated, during operation the mobile electronic device 325 will be carried, worn by or otherwise affixed to the user.

The electronic device 325 includes a processor 300, a transceiver 310, an antenna element 320, one or more input/output devices 330 (e.g., speaker/microphone, keypad, display/touchpad, electrical connectors, etc.), memory 340 and the sensors 110, 120. The sensors 110, 120 are incorporated therein and/or form part of the mobile electronic device 325 and are coupled to the processor 300 (directly or indirectly through other circuitry, such as the I/O devices 330). The sensors 130, 140 are physically external to the electronic device 325 and communicatively coupled to the electronic device 325 via a wired communication connection (e.g., electrical connector) and/or a wireless communication link 390.

The electronic device 325 may include other components, devices or functionalities, though not shown, and may also include fewer or more of the foregoing described elements.

The processor 300 may be a general purpose, special purpose or digital signal processor, and may be a plurality of processors or combination of such processors. The processor 300 includes functionality to perform signal coding, data processing, power control, input/output processing, and/or any other functionality enabling the electronic device 325 to operate in the system 100 and perform all or some of the process 200 including those functions described as being performed by one or more of the platforms or process 150, 180, 190.

The processor 300 is coupled to the transceiver 310 which is coupled to the antenna element 320. It will be understood that the processor 300 and the transceiver 310 may be separate components or integrated together. Similarly, the antenna element 320 may be a single element or a number of elements (multiple antennas or elements).

The processor 300 is also coupled to the one or more input/output devices 330 (including ports, busses, electrical connectors) operable for inputting/outputting data and signals. In addition, the processor 300 is coupled to memory 330 operable for storing and retrieving data, computer code, software, firmware and instructions. Any suitable type of memory storage device may be included, such as random-access memory (RAM), read-only memory (ROM), hard disk, subscriber identity module (SIM) card, a memory stick, a secure digital (SD) memory card, and the like.

FIG. 4 illustrates a flowchart of a process 400 in accordance with disclosed embodiments performed by the system 100 of FIG. 1. The process 400 illustrates one embodiment of an exercise management process contemplated by the present disclosure.

As shown, the process 400 includes the same (or similar) steps 202 thru 212 as illustrated in FIG. 2 and described above with respect to the process 200.

The generated biometric identifier(s) 160 and motion identifier(s) 170 are input to the context awareness platform 180 along with the exercise plan and activity 191a (step 414) and further processed.

The exercise plan 191a is generated from known exercise/fitness data or information, health normal information about various physical activities, and/or user-specific health information (as described more fully above). For example, the process may obtain exercise/fitness information and the user's health information (step 416) from external sources and databases, such as from the health data library 194 (cloud storage, local storage, online streaming, etc.). In addition, health normal information is obtained from various sources (as described above). Health data analysis and classification is performed (step 418). This step may classify the user into a medical/health category (or physical condition category) based on various factors. For example, the user may be classified as diabetic, high cholesterol, high blood pressure, or any other medical condition that may affect the user's health or wellness. In addition, the user may be classified into one or more physical categories, such as weak, strong, overweight, obese, male, female, etc. A determination of whether health data classification is complete is made (step 420).

If incomplete, then the process 200 reverts to step 416. If complete, then the health and action analysis platform 190 determines the exercise plan and activity 191a (step 422), and once determined, is input to the context awareness platform 180. The health and action analysis platform 190 obtains health research and medical information from various sources relating to common health rules, such as a person with high blood pressure should also have a high heart rate. The health and action analysis platform 190 gives rules to the exercise plan and activity classifier process 191 from which it determines the exercise plan and activity 191a (step 422) computed by the inputs from 190 and 194.

With the inputs shown, the context awareness platform 180 performs contextual data processing (step 426). Mapping between the received biometric/motion identifier(s) and the exercise plan and activity 191a is performed (step 428). For example, the context awareness platform 180 processes the data (exercise plan 191a and sensor identifiers 160, 170) and generates a mapping between the biometric identifier 160 and/or the motion identifier 170 and the exercise plan and activity 191a to determine an exercise recommendation. In another embodiment, the system may learn facts or behavior of the user, and the user exercise(s) recommended may be based at least in part on the user' past or learned behavior.

A determination of whether the exercise recommendation process is complete is made (step 430). If incomplete, the system reverts to step 414. If complete, the exercise recommendation process is performed by the exercise plan recommender 196 (step 432). The recommended exercise/plan 196a is delivered or notified to the user (e.g., through an I/O device in the mobile device, such as a display or speaker) or some other method of notification using the device.

It will be understood that the wellness management process 200 and the exercise management process 400 may be separately executed or executed in parallel or in conjunction with each other. Various modifications and variations to each process may be implemented, including combining portion(s) of the two processes into a global process.

In some embodiments, some or all of the functions or process(es) described herein and performed by the mobile electronic device 325 are implemented or supported by a computer program that is formed from computer readable program code and that is embodied in a computer readable medium. The phrase "computer readable program code" includes any type of computer code, including source code, object code, executable code, firmware, software, etc. The phrase "computer readable medium" includes any type of medium capable of being accessed by a computer, such as read only memory (ROM), random access memory (RAM), a hard disk drive, a compact disc (CD), a digital video disc (DVD), or any other type of memory.

It may be advantageous to set forth definitions of certain words and phrases used throughout this patent document. The terms "include" and "comprise," as well as derivatives thereof, mean inclusion without limitation. The term "or" is inclusive, meaning and/or. The phrases "associated with" and "associated therewith," as well as derivatives thereof, mean to include, be included within, interconnect with, contain, be contained within, connect to or with, couple to or with, be communicable with, cooperate with, interleave, juxtapose, be proximate to, be bound to or with, have, have a property of, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method for recommending an action to a user for enhancing wellness or health of the user, the method comprising:
   receiving first data from a first sensor configured to sense motion of a user;
   receiving second data from a second sensor configured to sense biometric data of the user;
   processing the received first and second data and identifying a type of activity engaged in by the user;
   determining a recommended action to be performed by the user in response to the identified type of activity and a current health/medical condition of the user; and
   notifying the user of the recommended action.

2. The method in accordance with claim 1 wherein processing and identifying further comprises:
   for different time periods, processing received data and identifying a type of activity for each of the different time periods.

3. The method in accordance with claim 1 wherein processing and identifying further comprises:
   storing historical activity information for the user.

4. The method in accordance with claim 1 wherein the current health/medical condition of the user comprises a medical condition known to the user, the medical condition has associated therewith a health risk and the identified activity will increase the health risk to the user.

5. The method in accordance with claim 1 wherein determining the recommended action to be performed by the user further comprises:
   determining the recommended action in response to one or more health/medical rules.

6. The method in accordance with claim 5 wherein the one or more health/medical rules are pre-stored in a health/medical database.

7. A method for recommending an action to a user for enhancing wellness or health of the user, the method comprising:
   receiving first data from a first sensor configured to sense motion of a user;
   receiving second data from a second sensor configured to sense biometric data of the user;
   processing the received first and second data and identifying a type of activity the user is currently conducting and a current physical condition of the user;
   determining a recommended action to be performed by the user in response to the identified type of activity and the current physical condition of the user; and
   notifying the user of the recommended action.

8. The method in accordance with claim 7 wherein the current physical condition of the user comprises a current medical/health condition.

9. The method in accordance with claim 8 wherein the current health/medical condition of the user comprises a medical condition known to the user, the medical condition has associated therewith a health risk and the identified activity will increase the health risk to the user.

10. The method in accordance with claim 7 wherein the current physical condition of the user comprises a condition occurring within the last day.

11. The method in accordance with claim 7 wherein processing and identifying further comprises:
   for different time periods, processing received data and identifying a type of activity for each of the different time periods.

12. The method in accordance with claim 11 wherein processing and identifying further comprises:
   storing historical activity information for the user.

13. A method for recommending a change in a user's current exercise activity for enhancing physical attributes and health of the user, the method comprising:
   receiving first data from a first sensor configured to sense motion of a user;
   receiving second data from a second sensor configured to sense biometric data of the user;
   processing the received first and second data and identifying a type of activity engaged in by the user and a current physical condition of the user;
   determining a recommended change to the user's current exercise activity in response to the identified type of activity and the current physical condition of the user; and
   notifying the user of the recommended change.

14. The method in accordance with claim 13 wherein the current physical condition of the user comprises a condition sensed by at least one of the first and second sensors during the user's current exercise activity.

15. The method in accordance with claim 14 wherein the condition sensed during the user's current exercise activity comprises heart rate.

16. The method in accordance with claim 13 wherein processing and identifying further comprises:
   for different time periods, processing received data and identifying a type of activity for each of the different time periods.

17. The method in accordance with claim 16 wherein processing and identifying further comprises:
   storing the identified type of activity for the different time periods.

* * * * *